(12) United States Patent
Liniger (10) Patent No.: US 7,766,874 B2
(45) Date of Patent: Aug. 3, 2010

(54) CATHETER HEAD COMPRISING A MOBILE CONNECTOR

(75) Inventor: Jürg Liniger, Ostermundigen (CH)

(73) Assignee: Roche Diagnostics International AG, Steinhausen (CH)

( * ) Notice: Subject to any disclaimer, the term of this patent is extended or adjusted under 35 U.S.C. 154(b) by 333 days.

(21) Appl. No.: 11/564,382

(22) Filed: Nov. 29, 2006

(65) Prior Publication Data

US 2007/0112303 A1  May 17, 2007

Related U.S. Application Data

(63) Continuation of application No. PCT/EP2005/005700, filed on May 27, 2005.

(30) Foreign Application Priority Data

Jun. 2, 2004 (DE) .................. 10 2004 026 806

(51) Int. Cl.
*A61M 5/178* (2006.01)
(52) U.S. Cl. ................. 604/164.01; 604/93.01; 604/161; 604/890.1
(58) Field of Classification Search ............ 604/167.06, 604/167.02, 167.01, 164.11, 533, 165.01, 604/272, 523, 240, 205, 110, 115, 93.01, 604/890.1, 27, 513, 164.01, 164.07, 181, 604/243
See application file for complete search history.

(56) References Cited

U.S. PATENT DOCUMENTS

| 4,692,146 A | * | 9/1987 | Hilger | .............. 604/288.01 |
|---|---|---|---|---|
| 4,755,173 A | * | 7/1988 | Konopka et al. | ........ 604/167.02 |
| 5,968,011 A | * | 10/1999 | Larsen et al. | ........... 604/288.02 |
| 7,083,597 B2 | * | 8/2006 | Lynch et al. | .................. 604/174 |
| 2002/0095138 A1 | | 7/2002 | Lynch et al. | |
| 2003/0130618 A1 | | 7/2003 | Gray et al. | |
| 2003/0216686 A1 | | 11/2003 | Lynch et al. | |
| 2004/0158207 A1 | | 8/2004 | Hunn et al. | |

FOREIGN PATENT DOCUMENTS

| EP | 0 239 244 A1 | 9/1987 |
|---|---|---|
| WO | WO 02/094352 A2 | 11/2002 |
| WO | WO 2004050148 A1 * | 6/2004 |

* cited by examiner

*Primary Examiner*—Nicholas D Lucchesi
*Assistant Examiner*—Jenner Yeh
(74) *Attorney, Agent, or Firm*—Dinsmore & Shohl LLP (57) ABSTRACT

A catheter head for medical and therapeutic applications including a catheter head housing, a cannula which protrudes from the catheter head and is to be introduced into organic tissue, a container connection for connecting a container containing a fluid to be administered, a fluid channel through which the fluid flows during the administration thereof, an injection needle connection for connecting an injection needle, a connection chamber which is adjacent to the cannula, the injection needle connection, and the fluid channel, and a connector that is arranged in a first position such that the injection needle can be guided from the injection needle connection into the connection chamber and then into the cannula, and in a second position such that it closes the connection chamber from the injection needle connection in a sealing manner after the injection needle has been removed.

25 Claims, 5 Drawing Sheets

CATHETER HEAD COMPRISING A MOBILE CONNECTOR

REFERENCE TO RELATED APPLICATION(S)

This application is a continuation of and claims priority to PCT Patent Application No. PCT/EP2005/005700, filed on May 27, 2005, which in turn claims priority to German Application No. 10 2004 026 806.1, filed on Jun. 2, 2004, the contents of which are incorporated in their entirety by reference herein.

BACKGROUND

The present invention relates to devices for delivering, administering, dispensing, injecting and infusing substances, and to methods of making and using such devices. More particularly, the present invention relates to a catheter head for medical, therapeutic and pharmaceutical applications or uses. In some embodiments, the catheter head can be part of an infusion set or can form an infusion set together with a catheter and/or one or more other elements conveying fluid. In some embodiments, the present invention may be used for the subcutaneous administration of a liquid medicament, for example insulin, and, in some embodiments, it may be used for self-administration.

Catheter heads that form part of an infusion set are known from the prior art. For example, EP 0 239 244 B1 discloses an injection set for subcutaneous injection. The core part of the injection set is a catheter head. This catheter head comprises a delivery line for the product to be injected, a flexible cannula protruding or extending from the catheter head, and a puncture needle attachment. To deliver or inject fluid into a patient, a puncture needle is guided through the puncture needle attachment into the catheter head and through the flexible cannula to insert the latter into the patient's tissue. The puncture needle pierces a septum on the puncture needle attachment. After the flexible cannula has been inserted into the patient's tissue by means of the puncture needle, the puncture needle is withdrawn from the catheter head. In this process, the septum on the puncture needle attachment seals the catheter head. A tight connection is thus established between the cannula in the tissue and a delivery means for the product. However, because of the septum on the puncture needle attachment being pierced, there is a danger of the connection not providing a complete seal. This applies especially when the septum on the puncture needle attachment is pierced several times.

SUMMARY

It is an object of the invention to improve the sealing of a catheter head and of a fluid delivery system comprising the catheter head.

In some embodiments, a catheter head according to the present invention for medical, therapeutic or diagnostic applications, and for pharmaceutical applications, comprises a catheter head housing, a cannula which is flexible, a fluid attachment, a fluid channel, a puncture needle attachment, a connection chamber, and a connector. The catheter head housing gives the catheter head its strength and holds the individual components of the catheter head together. It is possible for individual components of the catheter head to be integrated into the catheter head housing. The cannula protrudes or extends from the catheter head and, in the inserted state, extends into organic tissue. In some preferred embodiments, an area of the cannula is received in the catheter head housing. In such configurations, the cannula protrudes from the catheter head housing. However, it is also possible for the cannula to be applied tightly to an outer area of the catheter head. The fluid attachment of the catheter head serves for the attachment of a fluid delivery means which connects a container, containing a fluid to be administered, to the catheter head. The container can be designed, for example, as an ampule of a portable infusion device, but other configurations are also possible. As used herein, the term fluid is to be understood as a liquid product, although the fluid can also be gaseous. In some embodiments, to attach the container, the fluid delivery means is guided into the fluid channel and held with a form fit on the catheter head housing. In one preferred embodiment, the fluid delivery means comprises a delivery cannula with a connection needle. This needle is inserted into the fluid channel of the catheter head to establish a fluidic connection between the catheter head and the container. The fluid channel in the catheter head is a flow section of the catheter head through which the fluid flows during administration.

In some embodiments, the puncture needle attachment of the catheter head serves for attachment of a puncture needle. Through this attachment, the puncture needle is inserted into the catheter head housing and through the latter into the cannula. The puncture needle attachment can be open or can be closed by a soft material that can be pierced by the puncture needle. However, the puncture needle attachment itself has no sealing function after the puncture needle has been removed.

In some embodiments, the cannula, the puncture needle attachment and the fluid channel of the catheter head adjoin the connection chamber of the catheter head. The connection chamber forms a volume through which the fluid flows at least partially during the administration of the fluid. The geometry of the connection chamber can be rectangular, for example cuboid, although it can also be round or have an irregular shape. The abutments or connections, respectively, to the cannula, to the puncture needle attachment and to the fluid channel can be formed in the walls of the connection chamber. In some embodiments, the attachment for the cannula and the puncture needle attachment are facing each other in a straight line. In this case, the fluid channel adjoins the connection chamber at a remaining lateral chamber wall. The volume of the connection chamber can be kept constant during the insertion of the puncture needle and later during administration of the fluid, although the volume of the connection chamber can change or alter, and other components of the catheter head, e.g. the connector, can be moved into the connection chamber, respectively.

According to some embodiments of the present invention, the connector is mounted in the catheter head housing in such a way as to be movable between at least two different positions. In a first position, the connector is arranged in such a way that the puncture needle can be guided from the puncture needle attachment into the connection chamber and from there onward into the cannula. In the first position, the connector does not impede the puncture needle. The puncture needle at least does not pierce it. It also does not pass it, and the puncture needle and the connector have no contact in the first position of the connector. In a second position, the connector is arranged in such a way that it fluidically separates the cannula from the puncture needle attachment after the puncture needle has been removed, when the fluid delivery means is joined to the fluid attachment. It advantageously seals off the connection chamber to the puncture needle attachment. By means of the fluidic separation, the connector arranged movably on or in the catheter head housing creates a fluidically tight connection between the fluid delivery means and the cannula. For this purpose, a part of the connector or the connector as a whole is moved or displaced, relative to the catheter head housing, e.g. in the connection chamber.

In some embodiments, the connector can be of one-piece design. In other embodiments, it can be made of several parts. It can be made completely of one uniform material, or areas of it can be made from different materials. The connector has a round or square cross section, although other cross-sectional shapes are also possible.

In some preferred embodiments, the connector is locked in the second position. This increases the certainty of the connection chamber being tightly sealed off from the puncture needle attachment by the connector. The connector cannot then slip out of place. It is also possible that locking the connector in the second position will prevent reuse, by which a person using a catheter head could possibly become infected. In some preferred embodiments, the connector catches in the second position. For this purpose, the connector is provided with a blocking or locking device, for example a hook, at its end adjacent to the connection chamber, the blocking device preventing a return movement of the connector from the second position by an engagement, e.g. with a part of the catheter head housing. Instead of being provided on the connector, or in addition to being provided on the connector, a blocking element moving into blocking engagement to block the connector in the second position can also be provided on the catheter head housing.

In some preferred embodiments, the movement of the blocking element or blocking elements into the blocking engagement is effected by elasticity forces. However, the movement into the blocking engagement can also be effected by a gear mechanism which provides the relative movement between the connector and the catheter head housing into the blocking engagement. In the case of the elastically effectuated movement into the blocking engagement, a blocking element that is elastically tensioned until reaching the second position of the connector snaps automatically, because of its elastic restoring force, into engagement behind a matching blocking element and in this way blocks the connector against movement out of the second position.

In a preferred embodiment, the movement of the connector is a displacement of the connector. This displacement may be of a purely translatory nature. The catheter head housing and the connector form a sliding joint. However, it is also possible that this movement is superposed by a rotary movement or that the movement of the connector is exclusively a rotation movement. In such embodiments, the catheter head housing and the connector form a pivoting joint or, if appropriate, a sliding/pivoting joint. The rotary movement can, for example, be a tilting movement or a swiveling movement. The source of the movement of the connector may be a force that acts mechanically on the connector.

In some preferred embodiments, the catheter head housing guides the connector linearly along a movement axis during its movement. Upon attachment of the container, the latter's fluid delivery means is moved along the same axis relative to the catheter head housing. The catheter head housing forms a sliding guide for the connector, also for the fluid delivery means. For guiding the connector, it is advantageous if at least that part of the connector which is guided by the catheter head housing, and that part of the catheter head housing which is guiding the connector, each form hard sliding surfaces, i.e. are not made of a soft material which may be preferred for the formation of a hard/soft seal. If the connector has a soft area for the seal, this soft area should take up as little of the sliding surface of the connector as possible.

In some preferred embodiments, the catheter head housing guides the connector not just linearly along the movement axis, but also in a manner secure against twisting relative to this axis. This is of advantage if a passage of the connector, which in the second position connects the fluid channel formed by the connector to the cannula, is formed in a generated surface of the connector, as in some preferred embodiments. The securing against twisting is achieved by suitable shaping of the mutually guided generated surfaces of the connector and of the catheter head housing. The guiding can be achieved, for example, by a guide web engaging in a guide groove. However, it can also be obtained by means of a polygonal, e.g. rectangular, or oval external cross section of the connector, and by a generated inner surface of the catheter head being suitably adapted for the purpose of the twisting-free guidance.

In a preferred embodiment, the moving of the connector from the first position to the second position is coupled to the attachment of the fluid delivery means for the container. Without the container being attached, the connector is located in the first position. However, when the container is attached, the connector is automatically and inevitably located in the second position. The attaching effectuates the movement of the connector.

In a preferred embodiment, the connector in the first position protrudes beyond the catheter head housing in the area of the fluid attachment and, upon attachment of the fluid delivery means, is moved by said fluid delivery means into the second position. During the attempt to attach the fluid delivery means, it comes into contact with the connector and exerts a force on the latter. The connector is set in motion by this force and moves from the first position into the second position. The movements of the fluid delivery means and of the connector take place in the same direction during the attachment. The fluid delivery means thereby presses against the connector and thus effectuates its movement till the second position. A part of the fluid delivery means by this is pushed and/or turned into or onto the catheter head housing. The movement of the fluid delivery means ends at the moment when the fluid delivery means and/or the connector has reached an abutment. In a preferred embodiment, the reaching of this abutment is synchronized with the reaching of the second position of the connector.

According to a further preferred embodiment, the movement of the connector is coupled to the withdrawal of the puncture needle from the puncture needle attachment. The connector thus performs its sealing function immediately upon or after the withdrawal of the puncture needle from the puncture needle attachment.

In a further embodiment, the movement of the connector requires a separate actuation. This separate actuation can, for example, effectuate the movement of the connector in a mechanical and/or electrical manner.

In a preferred embodiment, the fluid channel is sealed off from the fluid attachment by a septum. This septum provides a tight and hygienic sealing of the fluid channel from the environment. The septum is pierced by means of a connection needle of the fluid delivery means, to establish the fluidic connection between the container and the fluid channel. The connector itself can form such a septum in one piece or can hold a separately formed septum.

In one preferred embodiment, the connector is designed as a hollow body. The cross section of the hollow space can be round, for example circular or oval, or can be polygonal, for example square, although the hollow body can also have an irregular shape.

In another preferred embodiment, the fluid channel extends within the connector and is accordingly moved along with a movement of the connector. The fluid channel can in this case extend completely or partially within the connector.

According to a preferred embodiment, the connector has a passage for the fluid, said passage being closed in the first position of the connector by a wall of the catheter head housing, the passage being open toward the cannula in the second position of the connector. In some preferred embodiments, the passage is situated at a location of the generated surface of the connector designed as a hollow body. The passage is located, in the second position, directly at the opening of the cannula to the connection chamber.

According to a further embodiment, the connector has an opening to the connection chamber in the first position. This opening is closed sealingly in the second position of the connector. This opening of the connector is located at its front end in the direction of movement. In the case of a symmetrical connector, one of its main axes runs or extends through this opening. In the case of a cylindrical connector, for example, the opening can cover the entire head surface of the cylinder. However, the opening can also take up only part of this area. In the second position of the connector, the opening directly adjoins the catheter head housing, and the sealing action is achieved by the seal between the catheter head housing and those surfaces of the connector surrounding the opening. Thereby, the seal is a hard/soft seal.

In a further embodiment of a catheter head according to the present invention, the fluid channel extends outside the connector, and the position of the fluid channel relative to the catheter head housing is unchangeable. In this case, the connector is compact and does not have any hollow spaces. However, this does not exclude the possibility of the connector having small indentations. When the connector is moved between its two positions, this has no effect at all on the position of the fluid channel relative to the catheter head housing. In some embodiments, the fluid channel is firmly integrated into the catheter head housing, i.e. the walls of the fluid channel are formed by the catheter head housing.

In some embodiments, the fluidic separation of cannula and puncture needle attachment can be achieved by a soft/soft seal. In the second position of the connector, however, a hard/soft seal is used for the fluidic separation of cannula and puncture needle attachment. This type of seal can advantageously be intensified by a suitable form-fit of the elements that are to be connected sealingly to one another. In some embodiments, the components may be pressed into or onto one another, which can be achieved, for example, by suitable shaping of the components.

In some embodiments, the connector can have a harder area and a softer area, the softer area providing the seal against the relatively harder catheter head housing in the second position of the connector. This softer area of the connector can be formed in different ways. The softer area can, for example, be designed around the circumference of the connector. The softer area can, for example, in partial areas be enclosed by the harder area. The softer area can also just have a simple cuboid shape. In all cases, the softer area comes into direct contact with the harder catheter head housing and effects a seal there.

In a preferred embodiment of the present invention, the catheter head comprises a cannula head which encloses the cannula on the connection chamber, the connector being made up of a hard main body and the cannula head being made of a softer material, so that, in the second position of the connector, a hard/soft seal is formed between the hard main body and the softer cannula head. The hard main body of the connector in this case has a passage which, in the second position of the connector, comes to lie above the cannula head in such a way that a fluidic connection between the cannula and the fluid channel in the connector can be established. The connector is in this case designed as a hollow body. If the catheter head housing forms the soft sealing part, the soft sealing part can also be a sealing insert or a coating with an opening which opening is connected to the cannula only via a further channel, however, on the other hand a cannula head provided directly at the upstream end of the cannula is the soft sealing part.

In a further embodiment of the present invention, the connector may be made of a soft sealing material. In this case, the entire connector is made from this soft sealing material. In principle, this connector can exert a sealing action at all places where it is in tight contact with a harder material. Moreover, such a connector is very easy to produce.

DETAILED DESCRIPTION

Figure 1A:
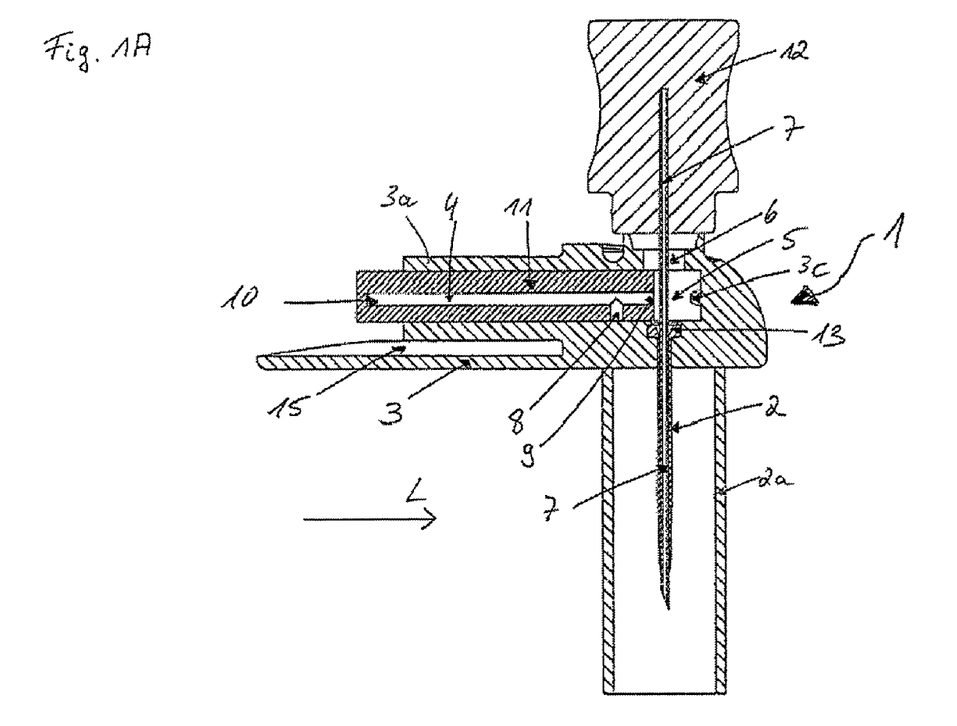
FIG. 1A a longitudinal section through one embodiment of a catheter head in accordance with the present invention with a puncture needle attached thereto, FIG. 1B a longitudinal section through the catheter head with attached fluid delivery means, FIG. 1C a rear view of the catheter head, seen from the fluid delivery means, FIG. 1D a cross section through the catheter head, FIGS. 2A-2B a longitudinal section through another embodiment of a catheter head in accordance with the present invention, FIGS. 3A-3B a longitudinal section through another embodiment of a catheter head in accordance with the present invention, FIGS. 4A-4B a longitudinal section through another embodiment of a catheter head in accordance with the present invention.

FIG. 1A shows a longitudinal section through a first embodiment of a catheter head 1 with a puncture needle 7 attached thereto. A housing 3 gives the catheter head 1 its strength and connects the individual components of the catheter head 1 to one another. On its underside, it forms an application face for application to the tissue surface, e.g. skin. In the central area of the catheter head 1, there is a cuboid connection chamber 5. At a top face, the connection chamber 5 opens into an puncture needle attachment 6. The puncture needle 7 with its puncture needle holder 12 is fitted on this puncture needle attachment 6. The puncture needle 7 protrudes or extends through the puncture needle attachment 6, the connection chamber 5, a cannula head 13 and through the cannula 2. In FIG. 1A, the cannula 2 and the puncture needle 7 situated therein are still enclosed by a protective sheath 2a, which is removed before use.

A connector 11 which is linearly displaceable in the direction of a movement axis L is designed as a hollow body in this embodiment. Its cavity forms a fluid channel 4 that extends in the direction of the movement axis L of the connector 11. The L axis extends at least substantially parallel to an underside of the catheter head housing 3 that rests on the skin during use. The connector 11 in FIG. 1A is located in its first position, so that the puncture needle 7 can be guided from the puncture needle attachment 6 into the connection chamber 5 and from there onward into the cannula 2, without touching or passing through the connector 11. The connector 11 has a passage 8 at one place on its jacket enclosing the fluid channel 4. At least around this passage 8, the connector 11 firmly rests against the catheter head housing 3. In this embodiment, the whole connector 11 is made of a soft material. The side faces of the connector 11 are in close contact with the harder material of the catheter head housing and form a soft/hard seal with the latter.

The catheter head housing guides the connector 11 along the L axis. The part of the catheter head housing guiding the connector 11 in its interior further guides with its outer surface a connection part of a fluid delivery means when this fluid delivery means is connected to the catheter head housing 3. Formed between the underside of the catheter head housing 3 and that part of the catheter head housing 3 forming the two guides, there is formed an insertion gap 15 which extends parallel to the L axis. An element of the fluid delivery means is inserted into this insertion gap 15 upon attachment of the fluid delivery means to the catheter head housing 3. The fluid attachment 10 is located at the left-hand end of the connector 11.

Figure 1B:
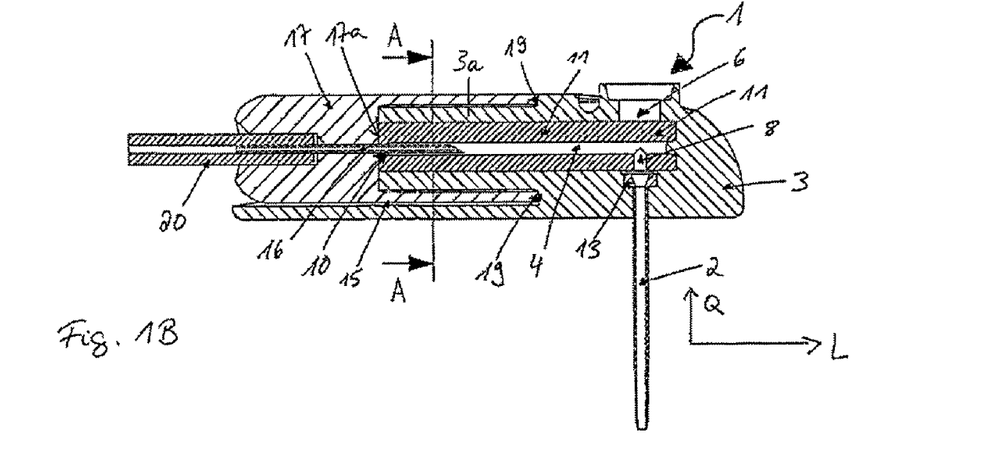

In FIG. 1B, the connector 11 is shown in its second position after removal of the puncture needle 7. Compared to the first position, the connector 11 has been pushed deeper into the catheter head housing 3 along the L axis, and at its right-hand end inside the connection chamber 5 abuts now directly against the catheter head housing 3. In this position, a projection 3c of the catheter head housing 3 projects into its opening 9 in order to improve the seal between the soft material of the connector 11 and the catheter head housing 3. The connection chamber 5 is now tightly sealed off from the puncture needle attachment 6 by the connector 11. A secure fluid connection is established between the fluid channel 4, the connection chamber 5 and the cannula 2. The fluid channel 4 opens out from the connector 11 through the passage 8 directly above the cannula head 13 of the cannula 2.

On the part of the fluid attachment 10, a connection needle 16 has been inserted in the direction of the L axis into the connector 11 and is sealingly enclosed by the material of the connector 11. In this example, the connection needle 16 protrudes from a delivery cannula 20 and, for safety reasons and for the purpose of connection to the catheter head housing 3, it is surrounded tightly by a connection needle holder 17 which is made of a rigid material and with which the delivery cannula 20 is also firmly connected. An area of the connection needle holder 17 directed toward the catheter head housing 3 is designed as an axially projecting circumferential wall that can be inserted into the insertion gap 15 of the catheter head housing 3 to the point of an abutment 19. An inner bearing face 17a of the connection needle holder 17 extending transverse to the L axis comes into contact with the connector 11 upon insertion of the connection needle holder 17. The connecting of the fluid delivery means (in one embodiment, comprising the connection needle 16, the connection needle holder 17, and the delivery cannula 20) is coupled to the movement of the connector 11 from the first position to the second position and synchronized in such a way that the connector 11 has reached the second position as soon as the fluid delivery means has been finally connected to the catheter head housing 3. The connection needle holder 17 comes, upon securing the fluid delivery means with the bearing surface 17a, with the connector 11 into contact and presses the connector 11 along the L axis into the catheter head housing 3 until the connector 11 firmly rests with its right-hand face against the catheter head housing 3. In this axial position of the connector 11, the passage 8 has also reached the cannula head 13, such that the fluid connection between the fluid channel 4 and the cannula 2 is established.

The catheter head housing 3, the connector 11 and the connection needle holder 17 are dimensioned such that the connection needle holder 17 in the direction of the L axis comes into abutment contact against the catheter head housing 3 when the passage 8 has reached the position in which it connects the fluid channel 4 to the cannula 2, and at the same time the sealing of the fluid channel 4 relative to the catheter head housing 3 by the connector 11 is established. In the connection operation, the catheter head housing 3 forms a plug, and the connection needle holder 17 a socket, which plug and socket are guided on one another. In this process, the connection needle 16 has been inserted through the soft material of the connector 11 in the direction of the L axis into the connector 11 and is connected to the fluid channel 4 located in the latter. Administration of a fluid product can now begin.

Figure 1C:
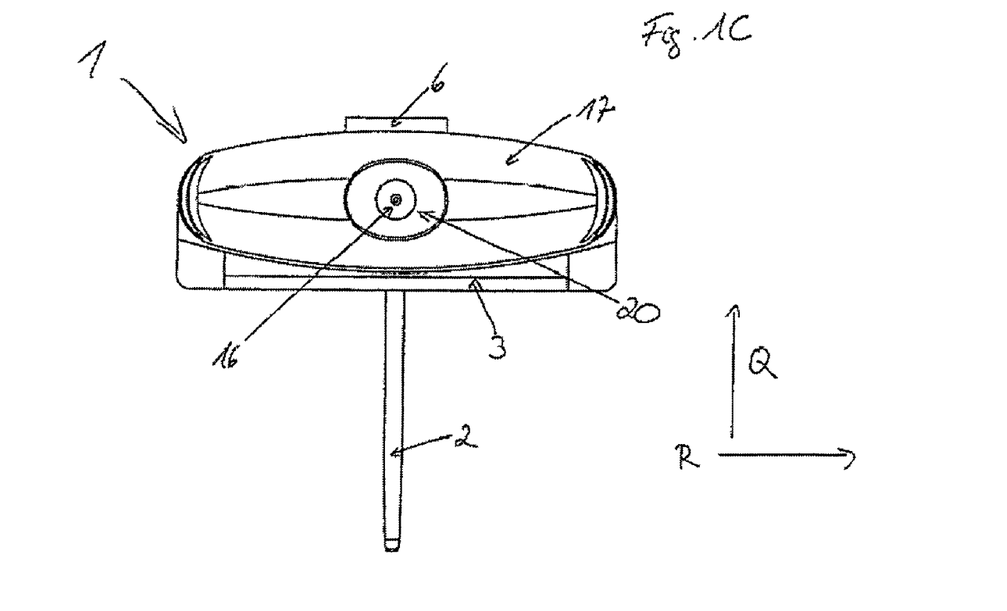

FIG. 1C shows a rear view of the catheter head 1 along a direction of view from the fluid attachment 10 in direction of the L axis. From the catheter head housing 3, the cannula 2 projects downward in the direction of the Q axis, which is perpendicular to the L axis. The puncture needle attachment 6 can be seen at the top. In the central area, the connection needle 16 is seen from the rear. It is surrounded by the delivery cannula 20. The delivery cannula 20, in which the connection needle 16 is located, is enclosed by the connection needle holder 17. In the rear view, the shape of the connection needle holder 17 is approximately elliptic. The underside of the connection needle holder 17 tightly abuts the catheter head housing 3. Instead of being guided via said plug/socket guide, or in addition to this, the connection needle holder 17 can also be guided, during connection, along its underside on the catheter head housing 3.

Figure 1D:
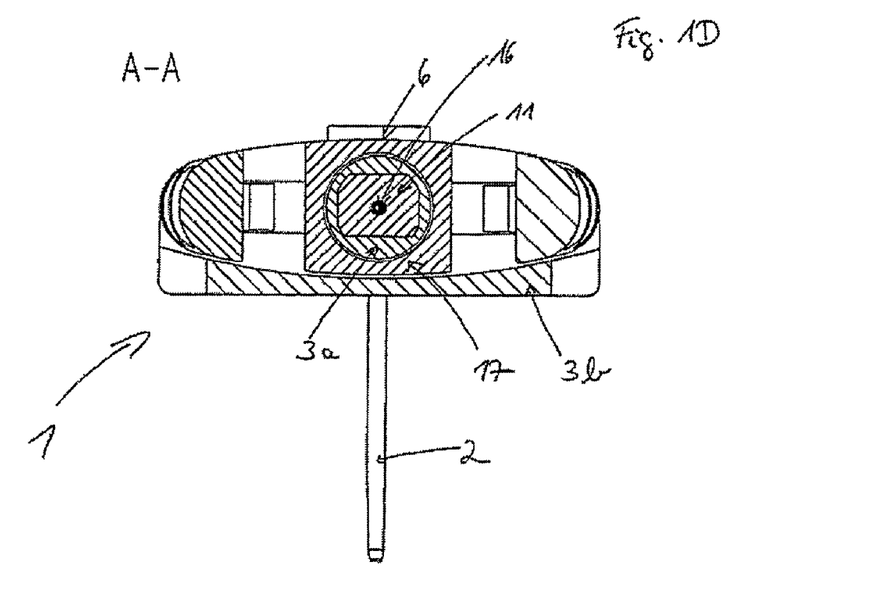

FIG. 1D shows a cross section through the catheter head 1, along the line A-A indicated in FIG. 1B. In the upper area, FIG. 1D ends with the puncture needle attachment 6, the cannula 2 projects downward from the catheter head 1. A lower bearing face 3b of the catheter head housing 3 can be seen, as well as in the central area the bordering 3a, which is formed around the connector 11. The connection needle holder 17 is inserted between the areas of the catheter head housing 3a and 3b. In the central area of FIG. 1D, the connector 11 can be seen, with the connection needle 16 located at its center. The edge areas of FIG. 1D show elements that serve to securely connect the connection needle holder 17 to the catheter head housing 3, they are designed in the form of locking hooks.

Figure 2A:
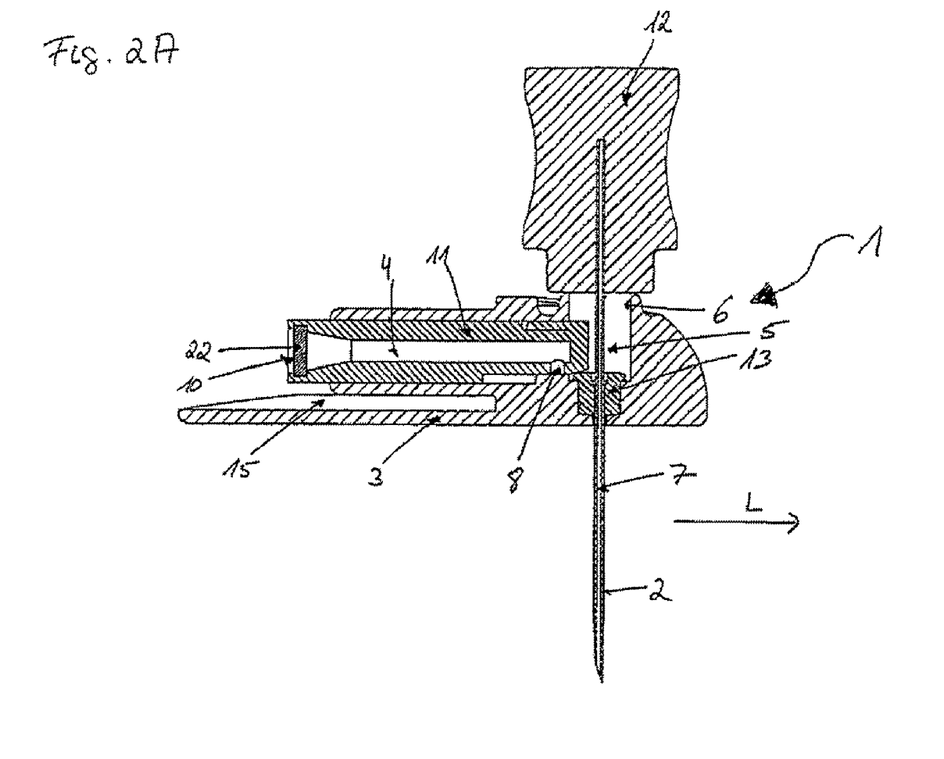

FIG. 2A shows another embodiment of the present invention. As in FIG. 1A, this is once again a connector 11 designed as a hollow body, which is shown in its first position. In the first position, in the same way as in the first embodiment, the connector 11 protrudes from the catheter head housing 3 in the area of the fluid attachment 10. Where no specific statements are made regarding the second illustrative embodiment, the statements regarding the first illustrative embodiment apply.

At the delivery side, in this embodiment, the connector 11 is closed by a separately produced septum 22 that is secured in the connector. In the direction toward the septum, the fluid channel 4 inside the connector 11 is widened in cross section in the area of the fluid attachment 10. In the area of the connector 11 adjacent to the connection chamber 5, there is no opening in this embodiment, i.e. the fluid channel 4 is closed there. In its area directed toward the cannula 2 adjacent to the connection chamber 5, the connector 11 has a passage 8 which, in the first position of the connector 11, is delimited by the catheter head housing 3. The connector 11 itself, except for the septum 22, is made of a hard material. The softer element for establishing a hard/soft seal with the connector 11 is formed by a cannula head 13, which is enlarged compared to the first embodiment.

Figure 2B:
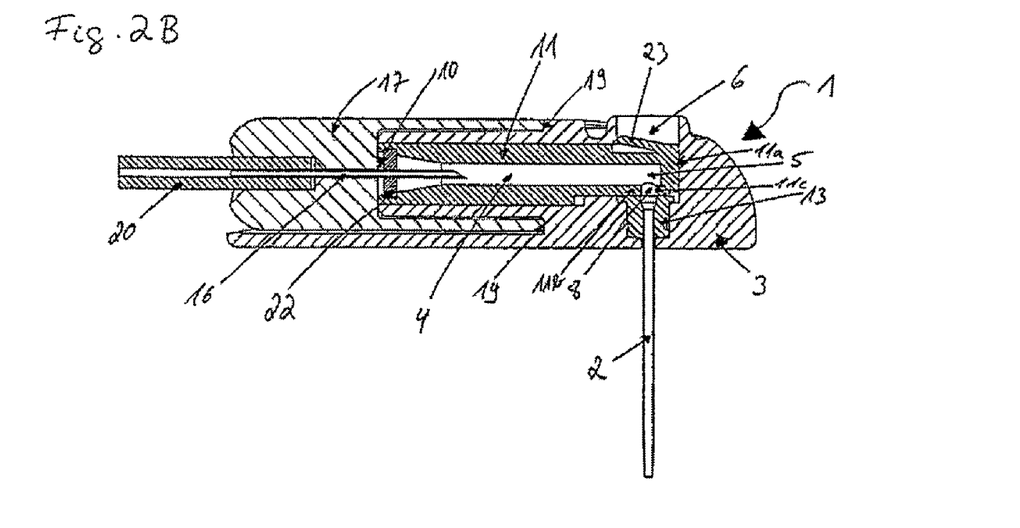

FIG. 2B shows the situation after removal of the puncture needle 7 during administration. A connection needle 16, which is firmly enclosed by a connection needle holder 17, has been attached to the fluid attachment 10 on the connector 11. The connection needle 16 here has pierced the septum 22 of the connector 11. The connector 11 is located in its second position. The attachment of the fluid delivery means to the connector 11 is coupled with the displacement of the connector 11 from the first position to the second position. The connection needle holder 17 has been inserted into the insertion gap 15 of the catheter head housing 3 until the connection needle holder 17 has been limited, in terms of its movement in the direction of the cannula 2, by the catheter head housing 3. In its second position, the connector 11 now also abuts in its front area 11$a$ the catheter head housing 3. The sealing action is accomplished by a hard/soft seal between the hard main body of the connector 11 and the softer cannula head 13. In the area around the passage 8, the connector 11 sealingly abuts the cannula head 13 in the areas 11$b$ and 11$c$. The flexible cannula 2 and the cannula head 13 can be formed together in one piece. They can also each be made of another material and connected, e.g. cohesively, to one another in a fluidtight manner.

The front area of the connector 11 is provided with a snap hook 23, which serves as a blocking or locking device and prevents inadvertent escape of the connector 11 from the second position. The blocking device 23 fastens itself in the area of the puncture needle attachment 6. In the first position of the connector 11, the snap hook 23 is pressed by the catheter head housing 3 in the direction of the connector 11, in the embodiment against a top face of the connector 11. The snap hook 23 is elastically tensioned in this state. As soon as the connector 11 has reached its second position, the connection position, the snap hook 23 comes free and spreads elastically and therefore automatically away from the connector 11. By this spreading action, it snaps in behind a wall of the catheter head housing 3 in the area of the attachment 6, which wall extends transverse to the direction of mobility of the connector 11, i.e. transverse to the L axis. The snap hook 23 thus blocks or prevents the connector 11 against moving from the second position in the direction of the first position. The blocking action is thus not cancelled out by withdrawal of the fluid delivery means. After use of the catheter head 1, the connector 11 blocks the cannula 2, for which reason no puncture needle 7 can be guided through the cannula 2, thus ensuring that, after use, the user cannot employ the catheter head 1 again because the connector 11 would be deliberately unblocked.

Figure 3A:
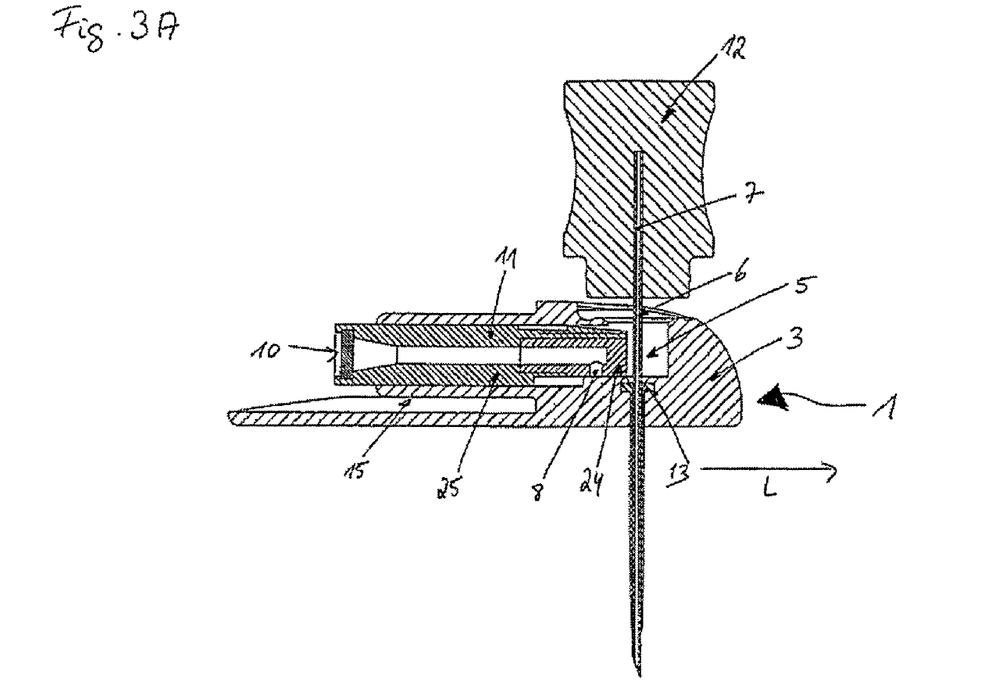
Figure 3B:
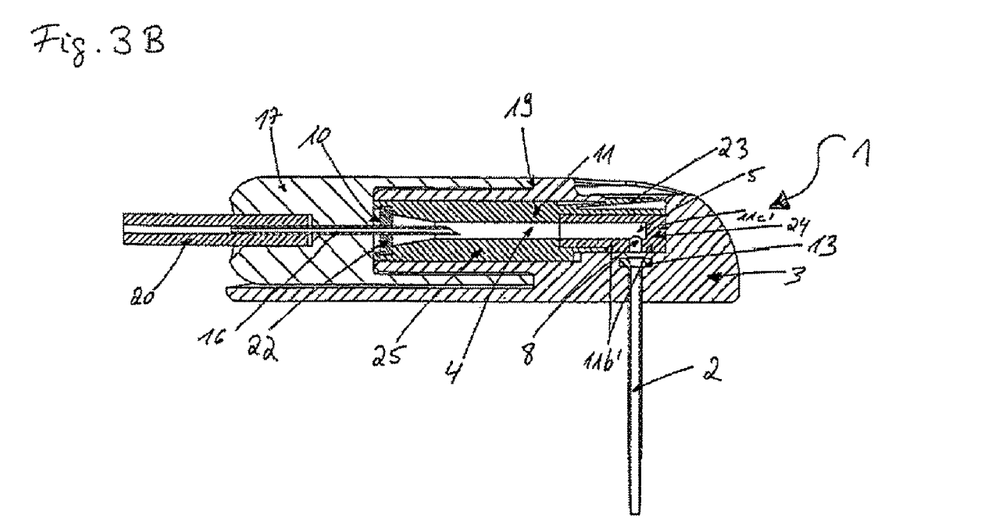

FIGS. 3A and 3B show another embodiment of the present invention. The connector 11 in this embodiment is made from two different materials. The connector 11 has a harder area 25 which extends across the central area of the connector 11 to the fluid attachment 10 and forms the sliding guide during the movement of the connector 11. An area 24 of the connector 11, directed toward the connection chamber 5, is made of a softer material. This softer area 24 surrounds the passage 8 and, in the second position of the connector 11, seals off the transition from the passage 8 to the cannula 2. In the outerlying area relative to the central longitudinal axis L of the connector 11, the softer area 24 is partially enclosed by the harder area 25. The connector 11 of this embodiment may be preferred to that of first embodiment because of the greater stability of the connector 11 and the reduced kinetic friction. The softer area 24 forming the seal can be designed as an insert part which is fitted with frictional engagement and tightly into the remaining harder part 25 of the connector 11. For example, the softer area 24 comprises silicone. The two areas 24 and 25 can also be formed together and cohesively connected directly upon primary forming of the connector 11, for example by multi-component plastic injection molding.

When the connector is moved into the second position, as shown in FIG. 3B, the softer area 24 of the connector 11 comes into sealing contact with the catheter head housing 3. This is the case both laterally in the area 11$c'$ of the connector 11 and also on the underside in the area 11$b'$. The catheter head shown in FIGS. 3A and 3B has, in its front area, a blocking or locking device 23 that securely locks the connector 11 in its second position. Apart from the described differences, the catheter head 1 of this embodiment generally corresponds to that of the second embodiment.

Figure 4A:
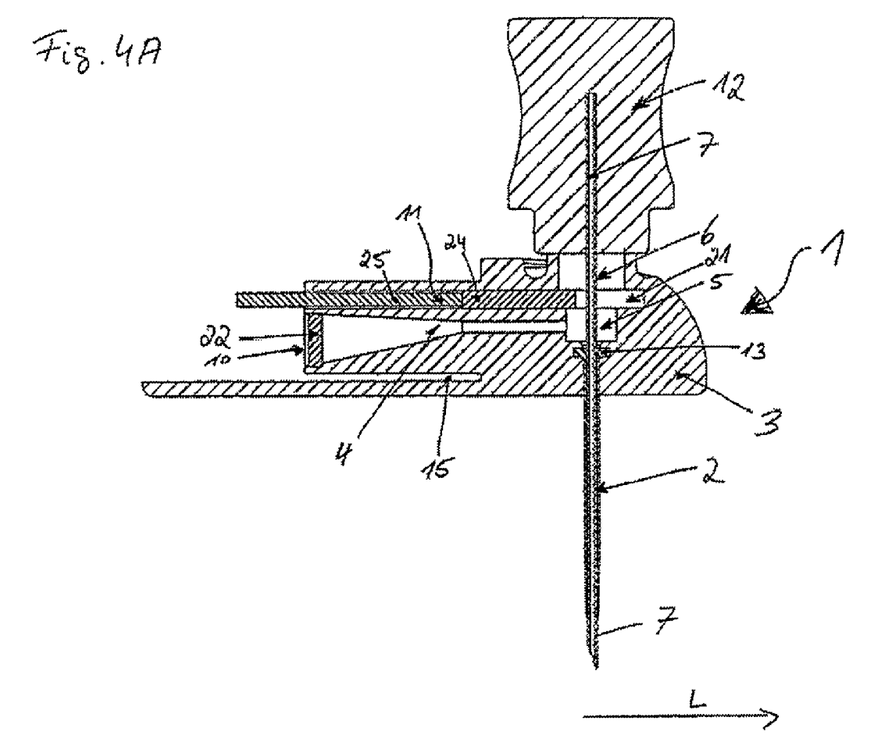
Figure 4B:
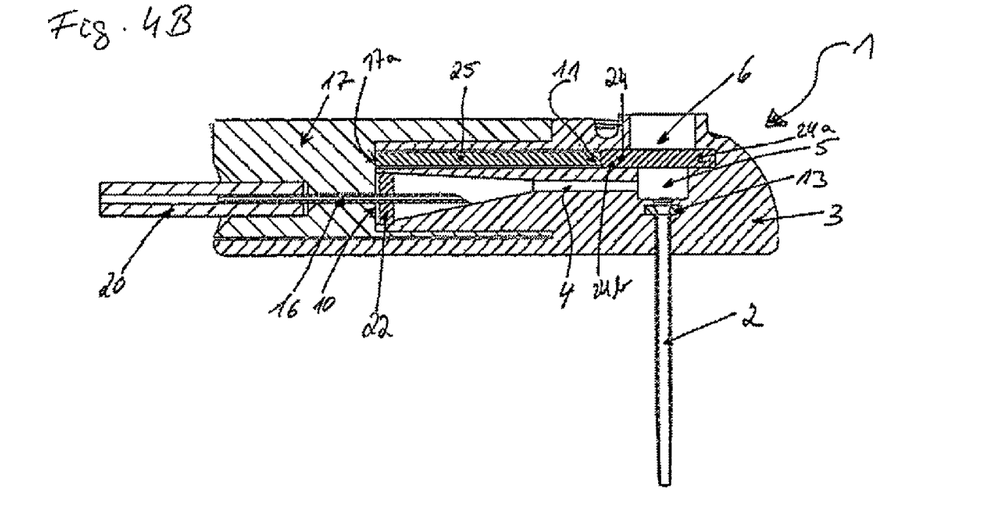

In FIGS. 4A and 4B, another embodiment of a catheter head 1 in accordance with the present invention is shown. In contrast to the preceding exemplary embodiments, the connector 11 is not designed as a hollow body. The fluid channel 4 is now not integrated in the connector 11, but instead is formed in the catheter head housing 3. Upon displacement of the connector 11, this fluid channel 4 does not move along with it, but remains in a fixed position relative to the catheter head housing 3. As also in the preceding examples, the fluid channel 4 formed in the catheter head housing 3 adjoins the connection chamber 5. Like also the fluid channel 4 of the first exemplary embodiment, it opens into the connection chamber 5. An area 21 of the connection chamber 5 extending deeper in the direction of movement of the connector adjoins the puncture needle attachment 6. The cannula 2 opens into the lower area of the connection chamber 5 with its cannula head 13.

In the first position of the connector 11 shown in FIG. 4A, the puncture needle 7, enclosed in the puncture needle holder 12, is guided through the puncture needle attachment 6 into the connection chamber 5 and through the latter into the cannula 2, to be able to insert the flexible cannula 2 into organic tissue. In this process, the connector 11 is not touched or penetrated. In the present example, the connector 11 is compact and designed substantially linearly as a plate structure. It has two axial areas of different hardness, a softer area 24 in the direction of the connection chamber 5, and a harder area 25 in the direction of the fluid attachment 10. In the first position of the connector 11, a part of the harder area 25 protrudes from the catheter head housing 3 counter to the direction of movement. Viewed from the underside, the catheter head housing 3 forms, above the fluid channel 4, a guide for the connector 11 to guide the latter in its movement from the first position to the second position and to seal the connection chamber 5 above the cannula 2 with the softer area 24 of the connector 11. The guide for the connector 11 again extends parallel to the longitudinal direction of the fluid channel 4.

When the fluid delivery means is attached to the catheter head housing 3, the connection needle 16 pierces the septum 22 and, in doing so, creates a connection between the delivery cannula 20 and the fluid channel 4. The connection needle 16 is enclosed in the connection needle holder 17. When the connection needle holder 17 is pushed onto the portion of the catheter head housing 3 that surrounds the fluid channel 4 and the connector 11, the connection needle holder 17 presses against the harder area 25 of the connector 11 in the direction of the axis L and moves the connector 11 in the direction of the axis L into its second position, as is shown in FIG. 4B.

Only the connector 11 is moved by this, the fluid channel 4 remains fixed. The softer area 24 of the connector 11 by this pushes itself in the connection chamber 5 into the recess 21 with an accurate form fit. In the areas 24a and 24b of the softer area 24, which are or come, respectively, in close contact with the by comparison harder catheter head housing 3, a soft/hard seal with the catheter head housing 3 is produced in each case. The connection chamber 5 is thus tightly sealed off from the puncture needle attachment 6. As in the other illustrative embodiments, in this case too, the movement of the connector 11 is coupled to the attachment of the fluid delivery means, i.e. it is effectuated by said attachment.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A catheter head for medical and pharmaceutical applications, comprising:
   a catheter head housing;
   a cannula, which extends from the catheter head for being inserted into organic tissue;
   a fluid attachment for attaching a fluid delivery means which delivers a fluid to be administered;
   a fluid channel through which the fluid flows during administration;
   a puncture needle attachment for attachment of a puncture needle;
   a connection chamber which adjoins the cannula, the puncture needle attachment and the fluid channel; and
   a moveable connector which, in a first position, is arranged on the housing such that a pathway defined by the puncture needle attachment, the connection chamber, and the cannula is substantially free of obstruction and a puncture needle can be guided from the puncture needle attachment into the connection chamber and from there into the cannula, and which, in a second position, is arranged on the housing such that said pathway is obstructed by the movable connector and the movable connector fluidically separates the cannula from the puncture needle attachment after the puncture needle has been removed.

2. The catheter head according to claim 1, wherein the connector is locked in the second position.

3. The catheter head according to claim 2, wherein the connector catches.

4. The catheter head according to claim 3, wherein at least one of the connector and catheter head housing is provided with a blocking device which prevents a return movement of the connector from the second position by means of engagement with the other one of the connector and catheter head housing.

5. The catheter head according to claim 4, wherein the blocking device comprises elements and wherein the movement of one element or of several elements into the blocking engagement is effected by an elasticity force.

6. The catheter head according to claim 5, wherein a movement of the connector is a displacement of the connector.

7. The catheter head according to claim 1, wherein the catheter head housing guides the connector in its movement in a linear manner along a movement axis in a manner secure against twisting.

8. The catheter head according to claim 1, wherein the movement of the connector from the first position to the second position is coupled to the attaching of the fluid delivery means.

9. The catheter head according to claim 1, wherein in the first position the connector extends beyond the catheter head in the area of the fluid attachment and, upon attaching of the fluid delivery means, is moved by the fluid delivery means into the second position.

10. The catheter head according to claim 1, wherein the fluid channel is sealed from the fluid attachment by a septum.

11. The catheter head according to preceding claim 1, wherein the connector forms a wall of the fluid channel and is a hollow body.

12. The catheter head according to claim 11, wherein the fluid channel extends within the connector and is moved along with a movement of the connector.

13. The catheter head according to claim 12, wherein the connector has a passage for the fluid which is connected to the fluid channel, the passage being closed in the first position of the connector and connecting the fluid channel to the cannula in the second position of the connector.

14. The catheter head according to claim 11, wherein in the first position the connector has an opening directed toward the connection chamber, and wherein this opening is sealingly closed in the second position of the connector.

15. The catheter head according to claim 1, wherein the fluid channel extends outside the connector through the catheter head housing.

16. The catheter head according to claim 1, wherein the connector has a harder area and a softer area, wherein the softer area effectuates the seal against the catheter head housing in the second position of the connector.

17. The catheter head according to claim 1, further comprising a cannula head which encloses the cannula at the connection chamber, wherein the connector consists of a hard main body and the cannula head of a softer material, so that, in the second position of the connector, a hard/soft seal is formed between the main body and the cannula head.

18. The catheter head according to claim 1, wherein the connector is made of a soft material.

19. A catheter head comprising:
   a housing;
   a cannula extending from the housing;
   a fluid attachment for attaching a fluid delivery means which delivers a fluid;
   a fluid channel through which the fluid flows;
   a puncture needle attachment for attachment of a puncture needle;
   a connection chamber which adjoins the cannula, the puncture needle attachment and the fluid channel; and
   a connector having two positions, a first position in which a puncture needle can be guided from the puncture needle attachment into the connection chamber and into the cannula and a second position in which the cannula is fluidically separated from the puncture needle attachment after the puncture needle has been removed.

20. The catheter head according to claim 19, further comprising a lock for releaseably securing the connector in one of said two positions.

21. The catheter head according to claim 20, wherein the connector has a harder area and a softer area.

22. The catheter head according to claim 21, wherein the softer area effectuates a seal against the housing in the second position of the connector.

23. A catheter head for medical and pharmaceutical applications which is connectable to a fluid deliverer comprising a connection needle holder, the catheter head comprising:

a catheter head housing, the catheter head housing defining an upper and a lower bearing surface and an insertion gap; wherein the insertion gap is configured to receive a portion of the needle connection holder;

a cannula, which extends from the catheter head for being inserted into organic tissue;

a fluid attachment for attaching the fluid deliverer;

a fluid channel through which the fluid flows during administration;

a puncture needle attachment for attachment of a puncture needle;

a connection chamber which adjoins the cannula, the puncture needle attachment and the fluid channel; and a moveable connector which, in a first position, is arranged on the catheter head housing such that a puncture needle can be guided from the puncture needle attachment into the connection chamber and from there into the cannula, and which, in a second position, is arranged on the catheter head housing such that it fluidically separates the cannula from the puncture needle attachment after the puncture needle has been removed, and wherein the upper and lower bearing surfaces of the catheter head housing are configured to guide the movable connector linearly and prevent twisting as the connector moves from the first position to the second position.

24. The catheter head of claim 23, wherein a cavity extending substantially the length of a longitudinal dimension of the movable connector defines the fluid channel.

25. The catheter head of claim 24, wherein a first end of the cavity defines the fluid attachment.

* * * * *